(12) United States Patent
Yamazaki et al.

(10) Patent No.: US 7,123,636 B2
(45) Date of Patent: Oct. 17, 2006

(54) LASER LIGHT IRRADIATOR

(75) Inventors: Iwao Yamazaki, Toyko (JP); Kimiyo Yamazaki, Tokyo (JP)

(73) Assignee: Ya-Man Ltd., Tokyo (JP)

( * ) Notice: Subject to any disclaimer, the term of this patent is extended or adjusted under 35 U.S.C. 154(b) by 0 days.

(21) Appl. No.: 10/491,000

(22) PCT Filed: Sep. 11, 2002

(86) PCT No.: PCT/JP02/09293

§ 371 (c)(1),
(2), (4) Date: Mar. 29, 2004

(87) PCT Pub. No.: WO03/028806

PCT Pub. Date: Apr. 10, 2003

(65) Prior Publication Data

US 2004/0246999 A1    Dec. 9, 2004

(30) Foreign Application Priority Data

Sep. 28, 2001 (JP) .............................. 2001-303773

(51) Int. Cl.
*H01S 3/00* (2006.01)
*A61N 5/06* (2006.01)

(52) U.S. Cl. ..................................... 372/38.07; 607/89

(58) Field of Classification Search .............. 372/38.1, 372/38.02, 38.03, 38.04, 38.07, 43, 29.01, 372/29.012, 29.014, 29.015, 29.021
See application file for complete search history.

(56) References Cited

U.S. PATENT DOCUMENTS

| | | | | |
|---|---|---|---|---|
| 4,232,678 A | * | 11/1980 | Skovajsa | 607/89 |
| 5,040,163 A | * | 8/1991 | Sasaki et al. | 369/116 |
| 5,272,716 A | * | 12/1993 | Soltz et al. | 372/109 |
| 6,168,589 B1 | * | 1/2001 | Tobinick | 606/9 |
| 6,558,653 B1 | * | 5/2003 | Andersen et al. | 424/49 |

* cited by examiner

*Primary Examiner*—Armando Rodriguez
(74) *Attorney, Agent, or Firm*—Bacon & Thomas

(57) ABSTRACT

A laser beam irradiation device according to the present invention is so constructed that it may increase or decrease the excitation electric current flowing through its semiconductor laser diode to enable a user to selectively practice both non-thermal and photo-thermal laser treatments.

CPU 41 is responsive to switching-on and -off of an output-power switching unit S2 for sending a reference signal to an amplifier 472 via an I/O port 44 and a D/A converter 471, so that the amplifier 472 may provide at its output terminals a reference voltage, with respect to which a control reference voltage for a desired laser output can be determined.

Semiconductor laser diode 35 radiates the laser beam from its opposite sides, and a photo-diode 473 receives one of the opposite laser beams to provide a light-accepting voltage at its output terminals. The so acquired light-accepting voltage is directed to an amplifier 474 for amplification, thereby obtaining the monitor voltage.

The reference voltage and the monitor voltage are applied to a differential amplifier 475, and a differential voltage is amplified by an amplifier 476. Thus a controlled working electric current is made to flow in semiconductor laser diode 35 so that it may be energized and oscillated at the set output level.

5 Claims, 7 Drawing Sheets

LASER LIGHT IRRADIATOR

TECHNICAL FIELD

The present invention relates to a laser beam irradiation device for projecting a laser beam to one's skin for beauty treatments such as skin treatment, removal of undesired hair and suchlike to make persons more beautiful.

BACKGROUND ART

When human skin is exposed to a laser beam under the skin temperature of 36 centigrade, on the skin caused is a certain vital reaction, which is called "non-thermal reaction". It includes photoelectric effect, photo-magneto effect, photo-dynamics effect, photochemical effect, photo-immunization effect, photo-zymogenesis effect and other such like optical effects.

Such non-thermal reactions are applied to body treatments such as slimming and hair restoration, since they stimulate blood circulation, body metabolism and the likes.

Also, when the skin is exposed to a laser beam, Joule heat is caused in the skin tissue by photothermal reaction to raise the temperature of the skin tissue.

The rise of the skin temperature causes various reactions such as; flashing, protein transformation, blood clot, vaporization, and carbonisation.

Such photothermal reactions are applied to beauty treatments such as: a skin beauty treatment, in which birth marks, stains, freckles and other unpleasing pigment cells are reduced into minute particles almost unnoticeable; and a depilation treatment, in which protein transformation is caused in hair root cells to destroy the regeneration mechanism of human hair.

These non-thermal and photothermal reactions can be selectively caused, depending on how much energy density a used laser beam has.

Referring to FIG. 7, a semiconductor laser diode is responsive to application of voltage for starting an electric current to flow, and at the outset it radiates natural light. A laser oscillation is caused when the so started electric current rises beyond a certain threshold value, and the laser output drastically increases in proportion to the increasing electric current, and accordingly the energy density of the laser beam increases.

The object of the present invention is to provide a laser beam irradiation device capable of giving both the non-thermal and photothermal treatments by controlling the amount of electric current excited in its semiconductor laser diode to adjust output power of the laser beam.

SUMMARY OF THE INVENTION

To attain this object, a laser beam irradiation device according to the present invention comprises:

a semiconductor laser diode for producing a laser beam;

a switching arrangement for changing the semiconductor laser diode in operation from one to another outputting state or vice versa; and a control circuit for controlling the amount of working current flowing in the semiconductor laser diode to adjust output power of the laser beam by using the switching means for an appropriate performance of either non-thermal or photothermal treatments.

The switching arrangement of the laser beam irradiation device is adapted to change the semiconductor laser diode between a high-outputting state and a low-outputting state.

The control circuit of the laser beam irradiation device which functions to make the working electric current flow and stop in the semiconductor laser diode at regular intervals, thereby projecting the laser beam intermittently.

The laser beam irradiation device wherein one shot of the intermittent radiation can be controlled in terms of the rotation angle of a rotary control.

DETAILED DESCRIPTION OF THE PREFERRED EMBODIMENT

The present invention is described below in respect of preferred embodiments.

Figure 1:
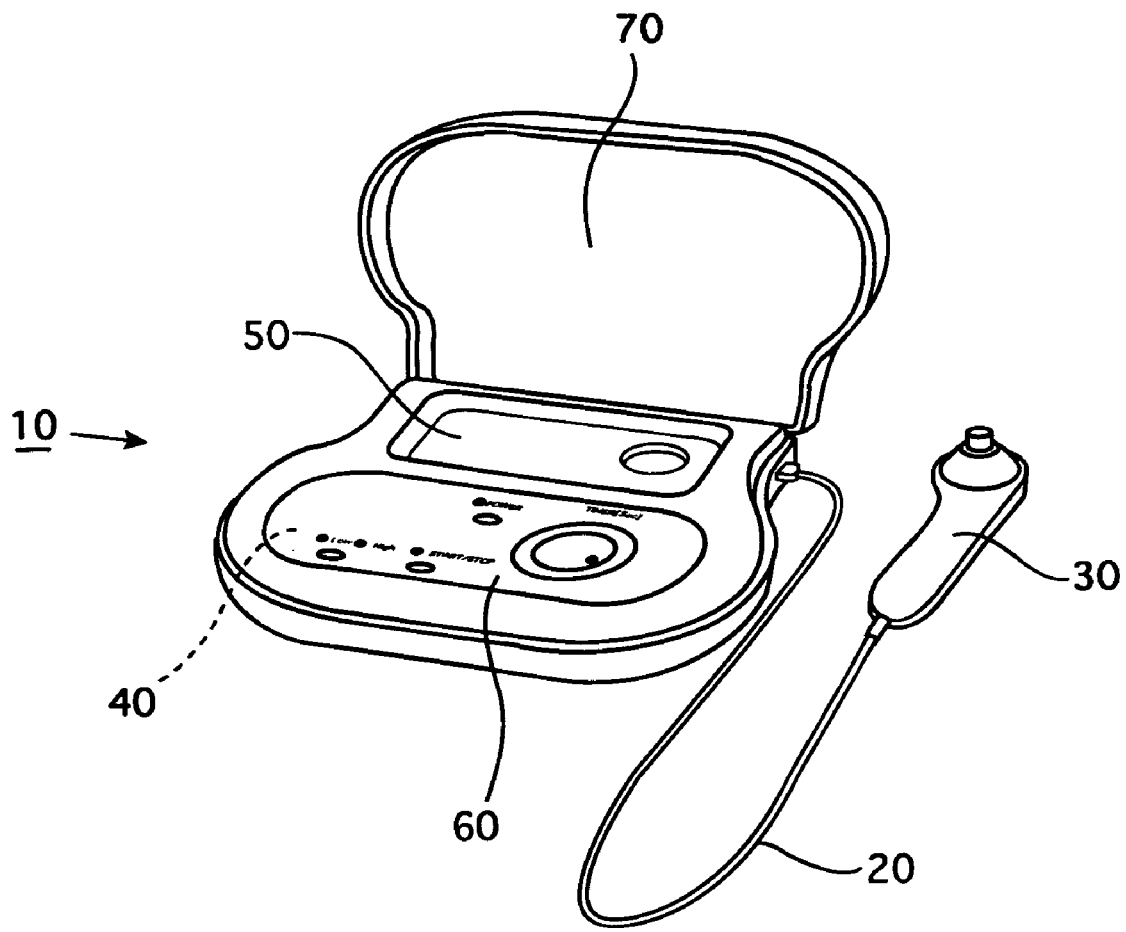
FIG. 1 is a perspective view of a laser beam irradiation device according to the present invention.

FIG. 1 shows how it looks in appearance.

The laser beam irradiation device comprises a major body 10 and an associated hand-held applicator 30 connected to the major body 10 via a given length of cable 20.

The major body 10 contains a control circuit 40, and the housing of the major body 10 has a recessed compartment 50 for accommodating the hand-held applicator 30 and a console 60 on its top surface, and a lid 70 hinged to one side of the housing.

Figure 2:
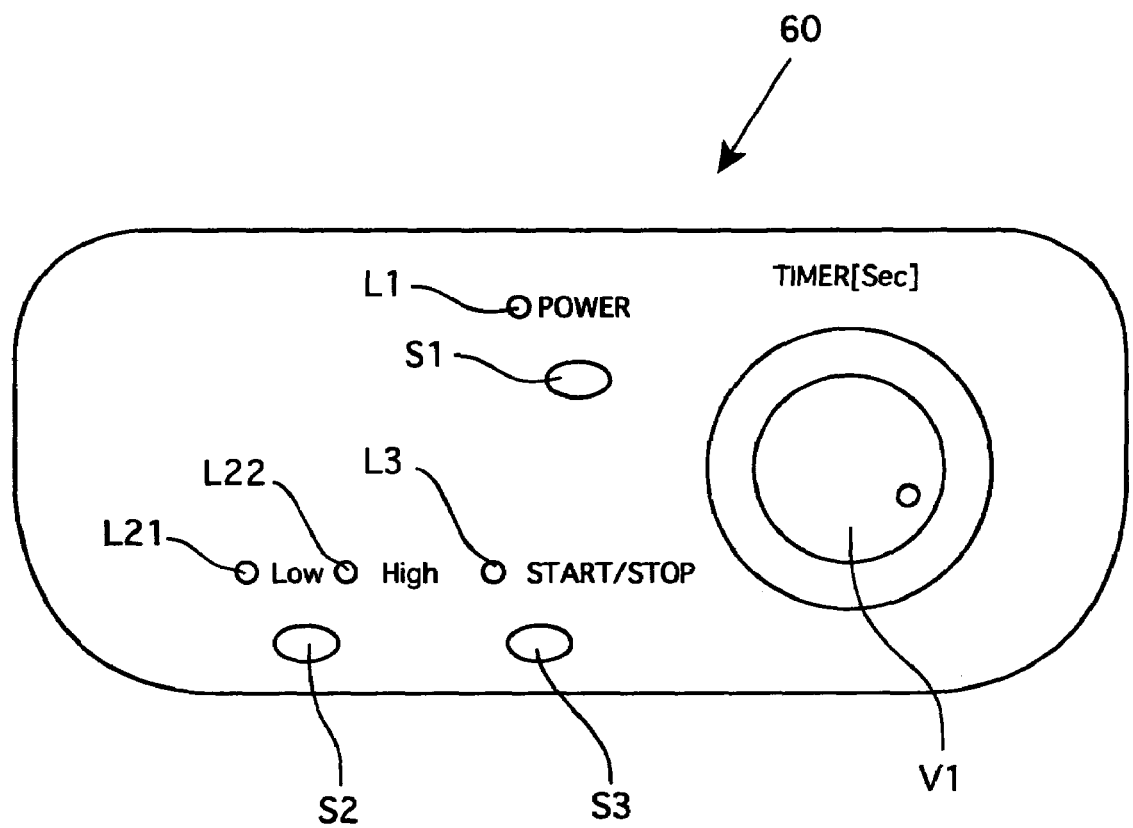
FIG. 2 is a front view of the console panel of the laser beam irradiation device.

FIG. 2 shows the console.

On the console 60 arranged are a power switch S1, an output-power switching unit S2, a standby switch S3 and a rotary radiation control V1, and further arranged are a power indicator LED L1 next to the power switch S1, a low-power indicator LED L21 and a high-power indicator LED L22 next to the output-power switching unit, and a standby indicator LED L3 next to the standby switch S3.

The power switch S1 functions to turn the power supply on and off (or put in or out of circuit), and accordingly the power indicator lamp L1 turns on and off respectively.

The output-power switching unit S2 functions to make the laser change in operation from a relatively low outputting state (for example 1.0 watt) to a relatively high outputting state (for example 1.6 watts) or vice versa.

Then, the low power indicator LED L21 turns on for the relatively low outputting state and turns off for the relatively high outputting state, whereas the high-power indicator LED L22 turns off for the relatively low outputting state and turns on for the relatively high outputting state.

The output-power switching unit S2 can work only when the standby switch S3 is off.

The initial output power of the laser beam is automatically set at the relatively low outputting state Lo in response to the turning-on of the power switch S1.

When the standby switch S3 is turned on, the laser is set on a standby condition for radiation and the standby indicator LED L3 turns on. When the standby switch S3 is turned off, the standby condition of the laser is cancelled and the standby indicator LED L3 turns off.

The mere switching-on of the power switch S1 keeps the laser stay in non-standby condition.

When the standby switch S3 is turned on, an associated timer starts counting to automatically turn off the standby switch S3 after a predetermined period (for example, 20 minutes) has passed irrespective of whether or not the laser has been radiated.

The rotary radiation control V1 is used to set a duration or dose of a single shot in the intermittent radiation in terms of its rotation angle, and the duration can change for example from one to nine seconds.

The rotary radiation control V1 can be operated to set a desired duration of each shot even if the standby switch S3 is on. The initial radiation dose when the power switch S1 is turned on is determined by the rotation angle of the rotary radiation control V1. The shot-to-shot interval in the intermittent radiation is determined (for example, 1.5 seconds) beforehand.

Figure 3:
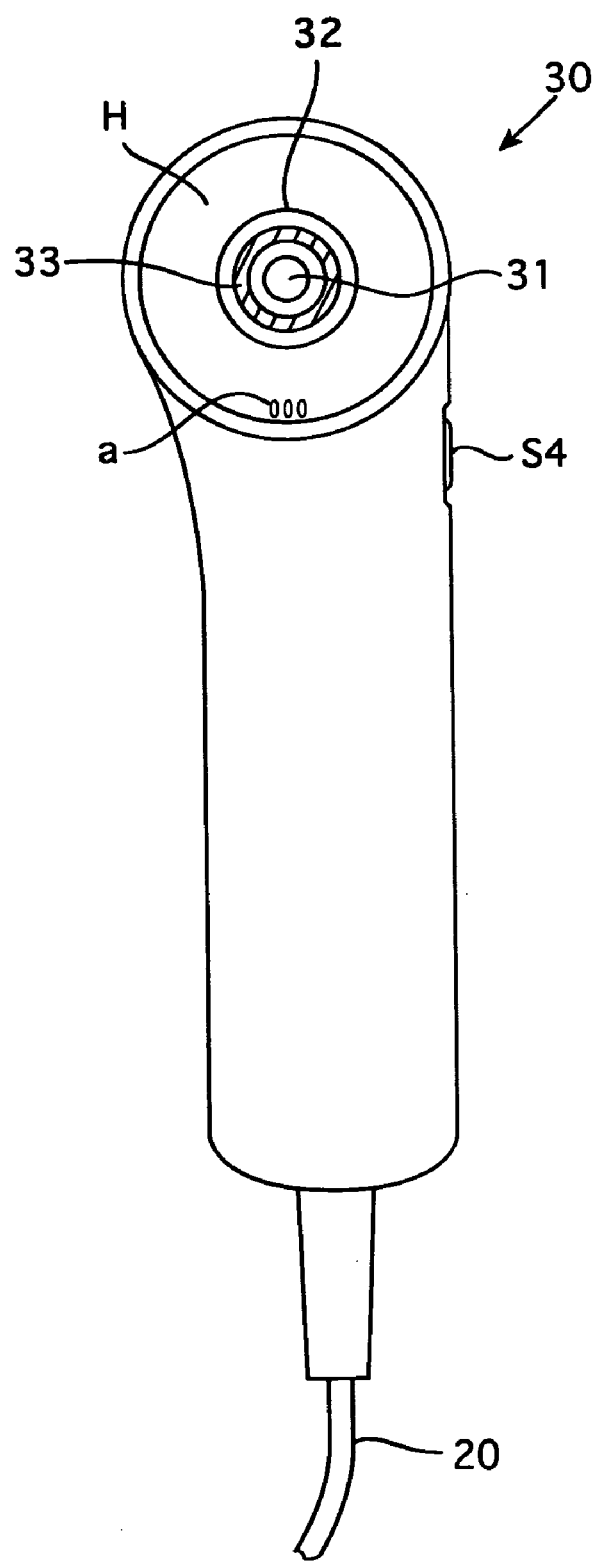
FIG. 3 is a front view of the hand-held applicator.
Figure 4:
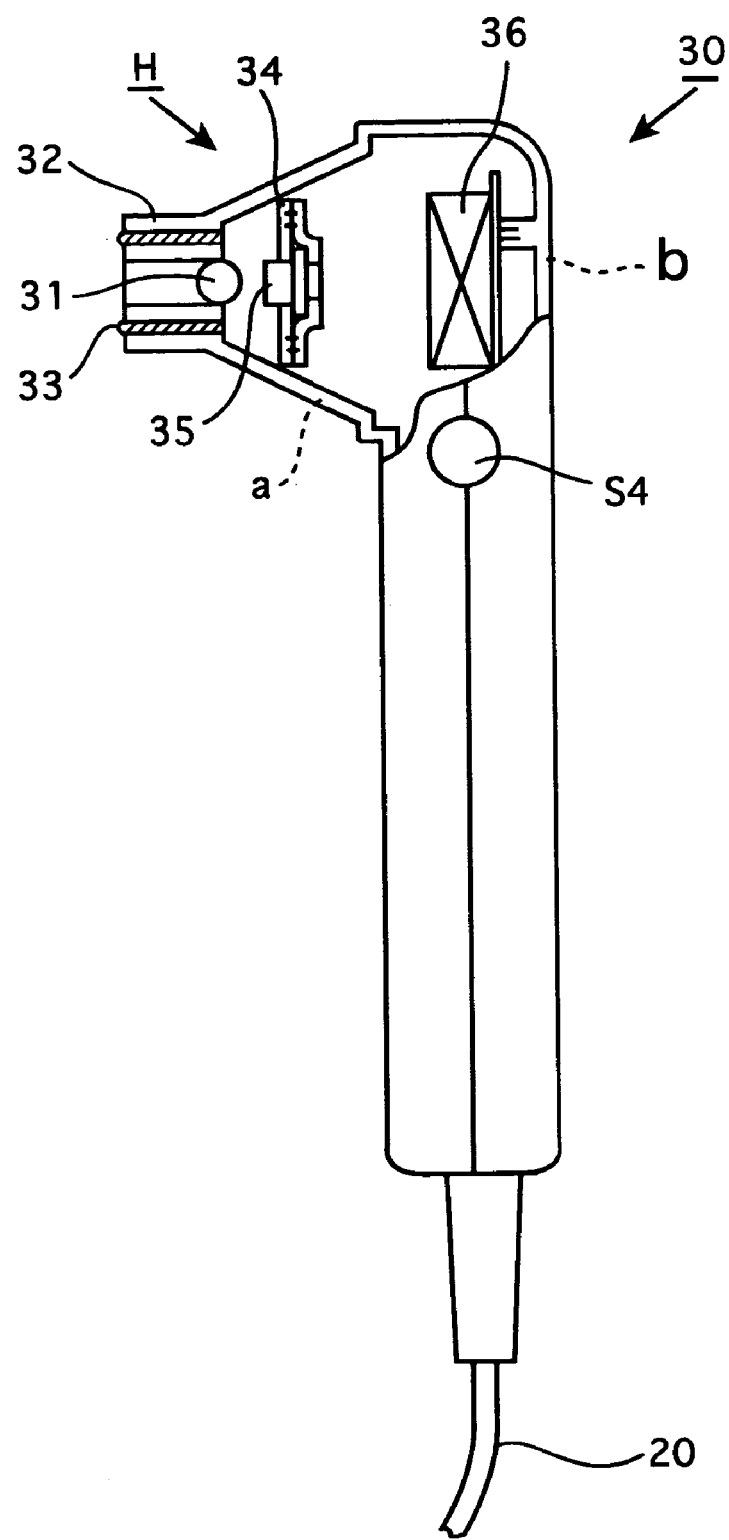
FIG. 4 is a side view of the hand-held applicator, partly in section.

Referring to FIGS. 3 and 4, the hand-held applicator 30 has a face H projecting laterally from its top, and a push button switch S4 on its side.

Also, the hand-held applicator has vent holes "a" and "b" at the lower part and on the rear side of the face H.

The face H has a spherical lens 31 press-fitted in its center hole, and the face H has a hollow cylinder 32 integrally connected to its circumference, encircling the spherical lens 31. The hand-held applicator 30 is applied to one's skin by the hollow cylinder 32 at its edge.

A coaxial cylindrical electrode 33 is embedded in the hollow cylinder 32 to project forward therefrom at its open edge.

A heat sink 34 is placed behind the spherical lens 31, and a semiconductor laser diode 35 is press-fitted in a through-hole bored in the center of the heat sink 34.

A cooling fan 36 is placed behind the heat sink 34.

The laser beam from the semiconductor laser diode 35 focuses on the focal point of the spherical lens 31 in the focal plane, in which the opening of the hollow cylinder 32 lies. The focal length of the spherical lens 31 is short enough to converge all the light energy to a limited spot, allowing the so converged beam to diverge beyond the focal point with the result that the light energy is distributed over the extensive area.

Accordingly the light energy density drastically decreases with the distance from the focal point, and therefore, there is little or no fear of injuring a living body even if it is exposed to the so dispersed light beam.

The heat sink 34 allows the heat generated by the semiconductor laser diode 35 to transmit therethrough. Thus, the semiconductor laser diode 35 is prevented from lowering its output.

The heat sink 34 is made of aluminum or aluminum alloy, whose thermal conduction is relatively high, and the heat sink 34 has further through holes made therein to effectively improve its heat radiation.

The semiconductor laser diode 35 may be a PN junction diode of GaAs or any other compound semiconductor, which can be excited by making an electric current flow therethrough for laser oscillation.

The peak-to-peak wavelength of the semiconductor laser diode is 600 to 1600 nm long, and the laser output ranged from 5 mW to 3 W, thereby efficiently causing a sufficient photothermal reaction on the skin.

Further caused are additional optical effects other than the required photothermal reaction, such as photoelectric effect, photo-magneto effect, photo-dynamics effect, photochemical effect, photo-immunizing effect, photo-zymogenesis effect and the like. The photo-biological activation expedites the body's metabolism and blood circulation under the skin. The laser beam is hardly absorbed by the water contents and blood, and therefore, it can reach deep under the skin.

Figure 5:
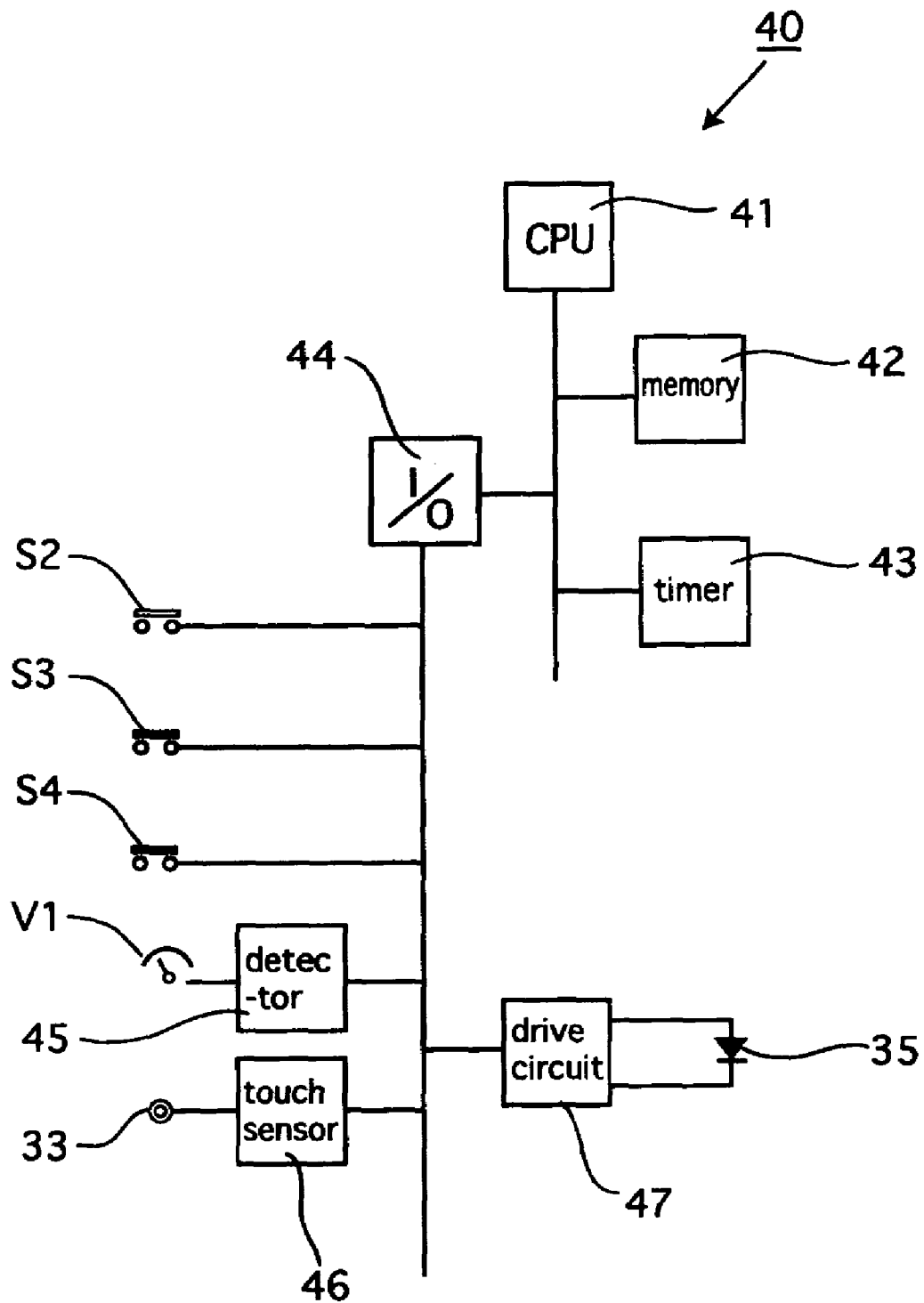
FIG. 5 is a block diagram of the control circuit.

FIG. 5 shows the control circuit of the laser beam irradiation device.

It comprises: a CPU 41 having a memory 42 and a timer circuit 43 both built therein; an output-power switching unit S2, a standby switch S3, a push button switch S4, a rotation angle detector 45 for determining the instantaneous rotation angle of the rotary radiation control V1, and a touch sensor circuit 46 for detecting the touching of the electrode 33 on the skin, all of which are connected on the input side of an I/O port 44; and a drive circuit 47 connected on the output side of the I/O port 44 for controlling the working current in the semiconductor laser diode 35.

The touch sensor circuit 46 comprises a high-frequency oscillator circuit and a switching circuit responsive to the working or non-working of the oscillator for turning on or off.

The electrode 33 is connected to one terminal of an oscillation coil of the oscillator circuit, and the oscillation stops as the electrode 33 touches the skin. The switching circuit is responsive to the stop of the oscillation for turning off.

The touch sensor circuit 46 may include an impedance element such as a capacitance or a resistance whose impedance drastically varies in response to the touching of the electrode to the skin, or may include a switching element or a piezoelectric element responsive to the touching of the electrode to the skin.

Figure 6:
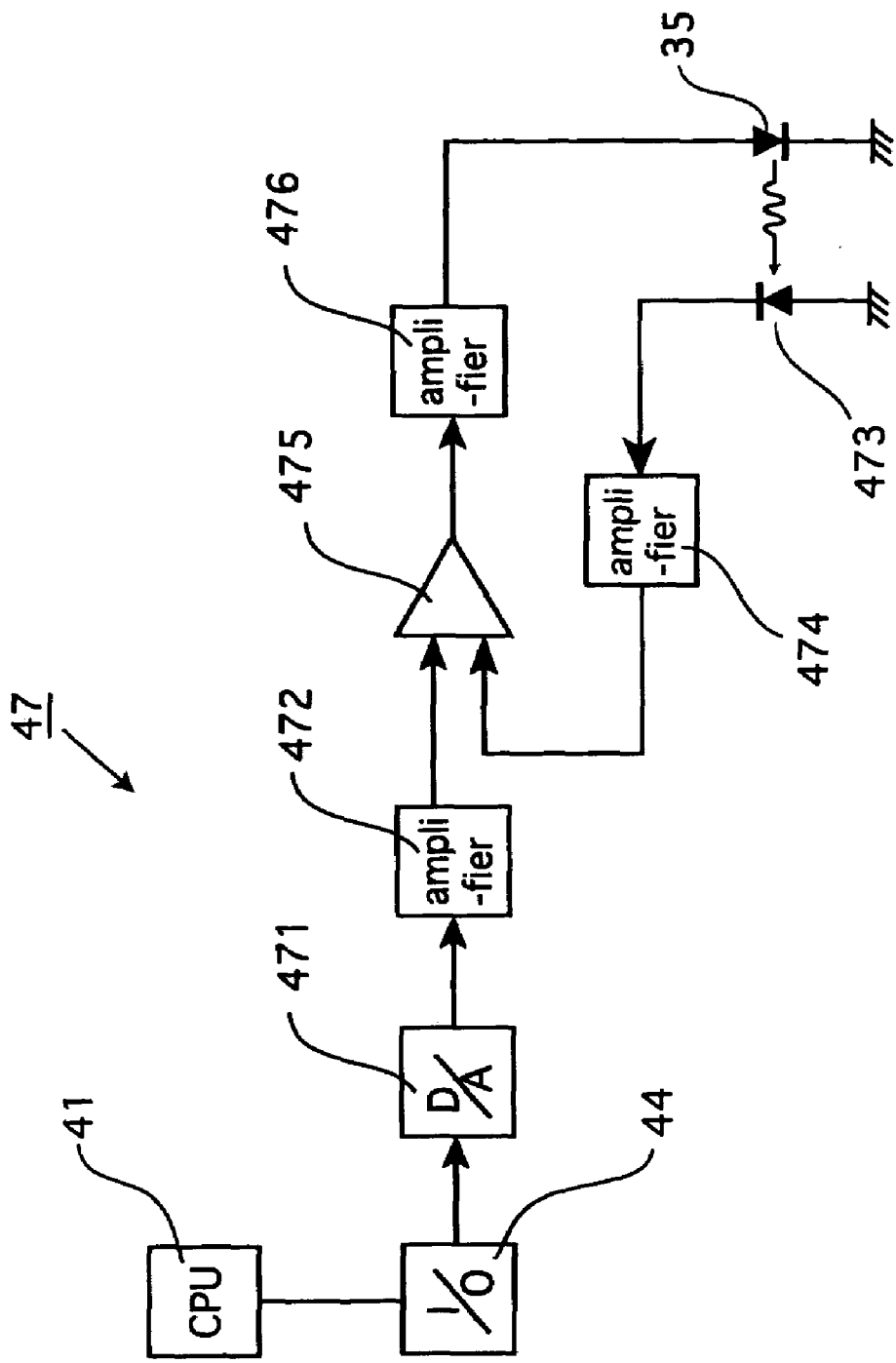
FIG. 6 is a block diagram of the drive circuit.
Figure 7:
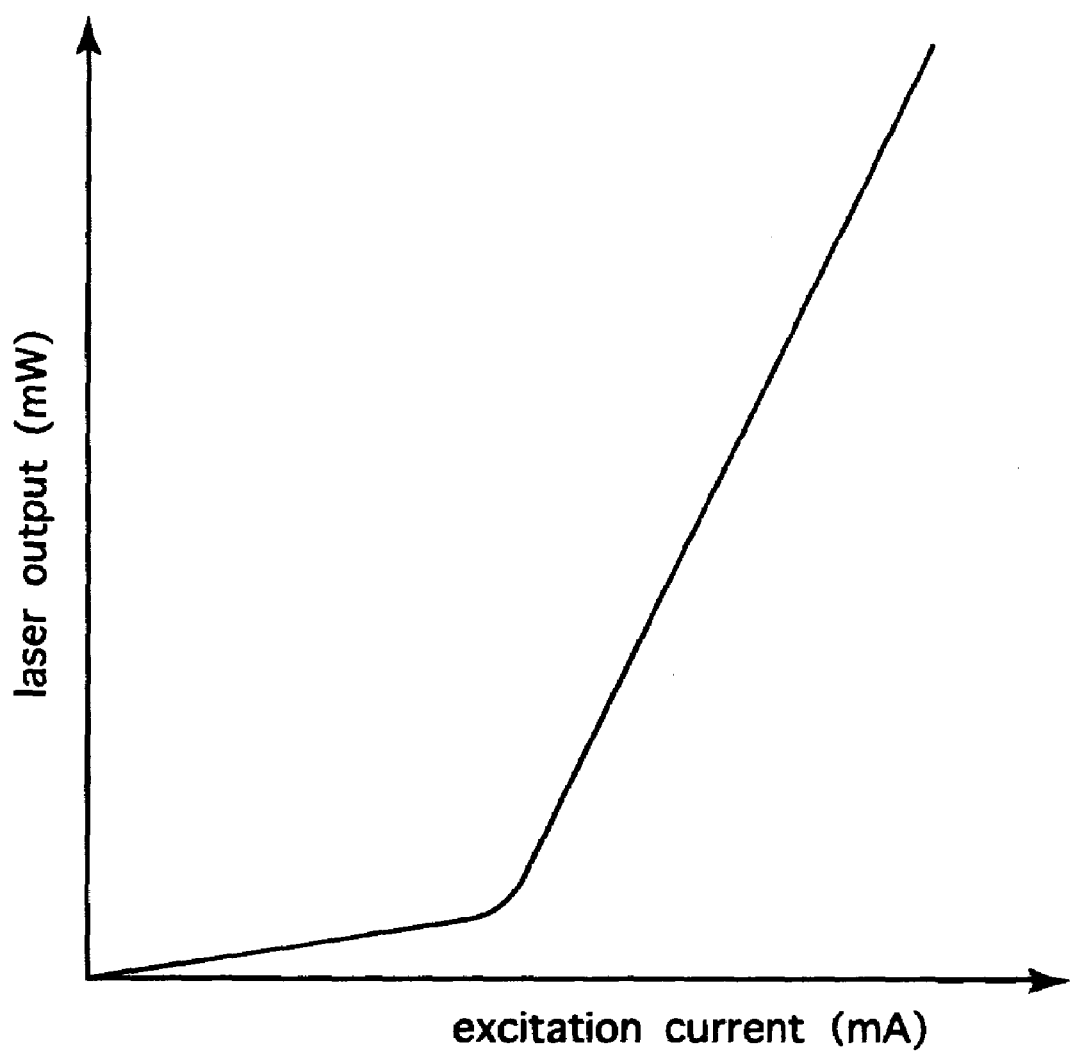
FIG. 7 is an excitation current-versus-laser output graph.

FIG. 6 shows a block diagram of the drive circuit 47.

The CPU 41 is responsive to the switching-on and -off of the output-power switching unit S2 for sending a reference signal to an amplifier 472 via the I/O port 44 and a D/A converter 471, so that the amplifier 472 provides at its output terminal a reference voltage, with respect to which a control reference voltage for a desired laser output is determined.

The semiconductor laser diode 35 radiates the laser beam from its opposite sides, and a photo-diode 473 receives one of the opposite laser beams to provide a light-accepting voltage at its output terminals. The so acquired light-accepting voltage is directed to the amplifier 474 for amplification, thereby obtaining the monitor voltage.

The reference voltage and the monitor voltage are applied to a differential amplifier 475, and a differential voltage is amplified by an amplifier 476. Thus a controlled working electric current is made to flow in the semiconductor laser diode 35 so that it may be energized and oscillated at the set output level.

The semiconductor laser diode can be thus switched to the relatively high- or low-powered oscillation Lo or Hi.

The CPU 41 carries out the on-and-off control of the working current from the drive circuit 47 under the control of the timer circuit 43.

The timer control includes two different modes, that is, the treatment time control in which the working current is made to flow a predetermined length of time for each treatment, and the radiation dose control in which the working current is made to flow a predetermine length of time for each shot in the intermittent radiation.

The duration of a single shot in the intermittent radiation can be set terms of the rotation angle of the rotary radiation control V1.

In carrying out a required beauty treatment with the so constructed laser beam irradiation device of the present invention, first the power switch S1 is turned on.

Then, the output-power switching unit S2 is turned on to select either the relatively low outputting state Lo for the non-thermal treatment or the relatively high outputting state Hi for the photothermal treatment.

Next, the rotary radiation control V1 is rotated to set the duration of a single shot in the intermittent radiation.

Next, the standby switch S3 turns on to put the device in the standby condition.

The hand-held applicator 30 is held in hand with the face H directed towards a selected spot on the skin at the angle of 90 degrees relative to the skin, and then, the electrode 33 of the cylinder 32 is pushed against the selected spot.

Then, the push button switch S4 is depressed to turn the semiconductor laser diode 35 on for predetermined seconds, and then turns off for prescribed seconds.

The semiconductor laser diode 35 turns on or off alternately, projecting onto the spot the laser beam of the required strength Lo or Hi, which is selected by the output-power switching unit S2.

A required beauty treatment is repeated as many times as required while moving the electrode 33 of the hand-held applicator 30 from place to place on the skin.

The radiation of the laser beam is made to stop in response to the electrode 33 being taken off from the skin, and the radiation of the laser beam is made to start in response to the electrode 33 being put on the skin.

Assuming that a fixed length of time has passed since the turning-on of the standby switch S3, it automatically turns off, thereby stopping the radiation of the laser beam.

INDUSTRIAL APPLICABILITY

As described above, the laser beam irradiation device of the present invention is responsive to the selection of the beauty treatment modes for appropriately increasing or decreasing the working electric current in the semiconductor laser diode. For that purpose, the output-power switching unit is designed to be selectively turned toward relatively high outputting state for photothermal treatment and toward relatively low outputting state for non-thermal treatment. This arrangement permits a safe and efficient beauty treatment as well as an expansion of the applicable scope of the laser beam irradiation device.

Radiation of the laser beam is intermitted at a fixed interval by controlling the working electric current in the semiconductor laser diode.

The shot duration of the laser beam can be controlled in terms of the rotation angle of the rotary radiation control.

In addition to the controlling of the power output of the laser, the energy density can be finely controlled in terms of the duration of beam radiation. This arrangement facilitates the sophisticated control of the laser output to meet a variety of beauty treatments as required.

The use of the rotary radiation control facilitates the controlling of the radiation of the laser beam.

The invention claimed is:

1. A laser beam irradiation device comprising:
   a semiconductor laser diode for producing a laser beam;
   a switching means for changing the semiconductor laser diode in operation from one to another outputting state or vice versa; and
   a control circuit for controlling the amount of working current flowing in the semiconductor laser diode to adjust output power of the laser beam by using the switching means for an appropriate performance of either non-thermal or photothermal treatments.

2. A laser beam irradiation device according to claim 1 wherein said switching means is adapted to change said semiconductor laser diode between a high-outputting state and a low-outputting state.

3. A laser beam irradiation device according to claim 1 wherein said control circuit functions to make the working electric current flow and stop in said semiconductor laser diode at regular intervals, thereby projecting the laser beam intermittently.

4. A laser beam irradiation device according to claim 3 wherein said control circuit includes a rotary control, and wherein intermittent projecting of the laser beam radiation is controlled in terms of the rotation angle of said rotary control.

5. A laser irradiation device according to claim 1, wherein said switching means includes a power switch, said switching means being such that when said power switch is turned on said switching means maintains said semiconductor laser diode at the same output state, and said switching means being actuated to change the output sate of said semiconductor laser diode thereafter.

* * * * *